US00PP10090P

United States Patent [19]

Challet

[11] Patent Number: Plant 10,090

[45] Date of Patent: Oct. 28, 1997

[54] CHRYSANTHEMUM PLANT NAMED 'CHAZAMI'

[75] Inventor: Jean Pierre Challet, Nuaille, France

[73] Assignee: Selection New Plant Sarl, Le Luc, France

[21] Appl. No.: 773,722

[22] Filed: Dec. 24, 1996

[51] Int. Cl.[6] ..... A01H 5/00

[52] U.S. Cl. ..... Plt./82.3

[58] Field of Search ..... Plt./74.1, 82.2, Plt./82.3

*Primary Examiner*—Howard J. Locker

*Attorney, Agent, or Firm*—Burns, Doane, Swecker & Mathis, L.L.P.

[57] ABSTRACT

A new and distinct Chrysanthemum cultivar named 'Chazami' is provided. The new cultivar was the result of a controlled breeding program. Attractive golden yellow double daisy blossoms are formed in profusion as a round ball surrounding the plant. Flower production is carred out on a natural production cycle. The plant possesses strong stems, forms attractive leaves, and commonly assumes a height of approximately 35 to 40 cm. The blossom coloration contrasts nicely with the dark green foliage. The new cultivar is particularly well suited for use in the prodution of a decorative pot Chrysanthemum. No growth regulator is necessary to achieve the short plant height.

1 Drawing Sheet

SUMMARY OF THE INVENTION

The present invention comprises a new and distinct cultivar of Chrysanthemum, botanically known as *Dendranthema grandiflora,* and hereinafter is referred to by the cultivar name 'Chazami'.

The new cultivar is the product of a planned breeding program which had as its objective the creation of a new Chrysanthemum cultivar that is intended primarily for pot mum production.

The breeding program which resulted in the production of the new cultivar of the present invention was carried out in a controlled environment during November, 1987, at Nuaille, Trementines, France. The female parent (i.e., the seed parent) was the '8327-2' cultivar (non-patented in the United States and never even offered for sale in France) having yellow flower, poor foliage, and a tall plant height, and the male parent (i.e., the pollen parent) was the '8454-9' cultivar (non-patented in the United States and never even offered for sale in France) having attractive glossy foliage. The parentage of the new cultivar can be summarized as follows:

'8327-2'×'8454-9'.

The seeds resulting from the above pollination were sown and many small plants were obtained which were physically biologically different from each other. Selective study resulted in the identification of a single plant of the new cultivar.

It was found that the new cultivar of the present invention:

(a) exhibits in profusion attractive golden yellow double daisy blossoms,
(b) is highly amenable to branching by pinching,
(c) forms attractive dark green foliage,
(d) assumes a short plant height, and
(e) is particularly well suited for pot mum production on a natural production cycle.

The new cultivar is intended primarily as a decorative pot double daisy chrysanthemum for growing outdoors at temperatures above freezing. However, the new cultivar also can be grown indoors.

In the absence of debudding approximately 3 to 6 blossoms commonly form per stem. Additionally, the new cultivar can be grown as a disbud to form striking blooms. An increased number of branches readily can be induced by pinching. The pinching of a cutting commonly produces approximately 8 to 10 stems per cutting. No growth regulator is required to produce the short plant height; however, a growth regulator optionally can be utilized.

The new cultivar can be considered to be an October-flowering greenhouse variety with the natural flowering season commonly occurring in weeks 42 to 43 of the year. The blossoms are long lasting and commonly can be maintained on the plant for approximately three weeks.

Asexual reproduction of the new cultivar by cuttings initially taken during 1988, as performed in Nuaille, Trementines, France, in a controlled environment has demonstrated that the characteristics of the new cultivar as herein described are firmly fixed and are retained through successive generations of asexual propagation.

'Chazami' has not been observed under all possible environmental conditions to date. Accordingly, it is possible that the phenotype may vary somewhat with variations in the environment, such as temperature, light, day length, contact with pesticides and/or subjection to growth retardant treatments.

The new 'Chazami' cultivar is being marketed under the Aurea trademark.

BRIEF DESCRIPTION OF THE PHOTOGRAPH

The acompaning photograph was prepared during March, 1996, and shows as nearly true as it is reasonably possible to make the same in a color illustration of this character, typical plants and plant parts of the new cultivar of the present invention. The plants were 12 weeks of age and were grown in Nuaille, Trementines, France, under standard greenhouse conditions which approximate those commonly utilized for the production of decorative pot mums. The plant had been pinched once and had not been disbudded. No growth regulator was utilized.

DETAILED DESCRIPTION

Figures 1, 2, 3, 4, 5, 6, 7, 8, 9, 10, 11, 12, 13, 14:
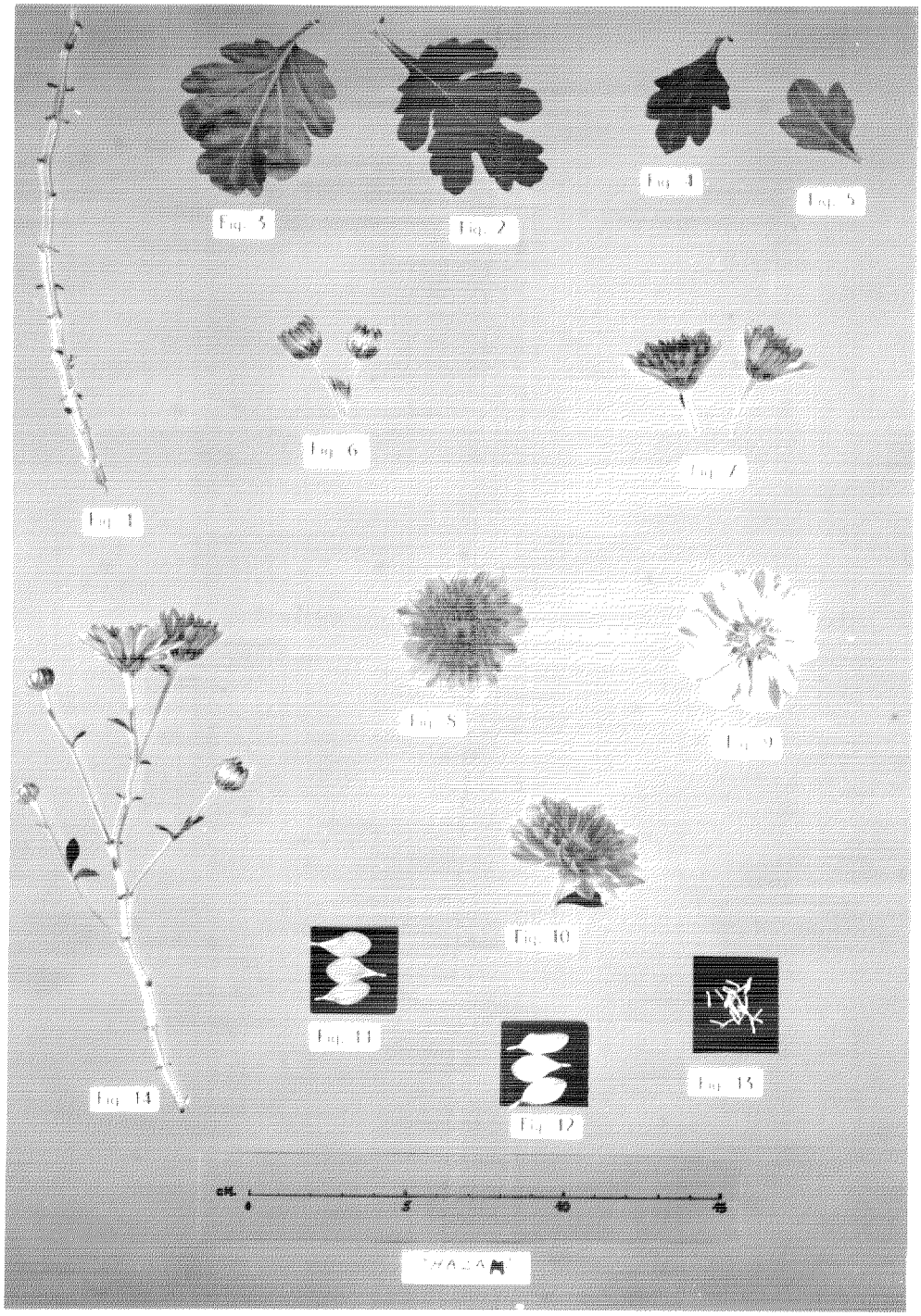
FIG. 1 illustrates a typical stem.
FIG. 2 illustrates a top view of a typical leaf from the lower part of the stem.
FIG. 3 illustrates an under view of a typical leaf from the lower part of the stem.
FIG. 4 illustrates a top view of a typical leaf from the upper part of the stem.
FIG. 5 illustrates the under view of a typical leaf from the upper part of the stem.
FIG. 6 illustrates the side view of a pair of largely unopened buds.
FIG. 7 illustrates the side view of a pair of typical flowers in the course of opening.
FIG. 8 illustrates the top view of a typical open flower.
FIG. 9 illustrates the under view of a typical open flower.
FIG. 10 illustrates the side view of a typical open flower.
FIG. 11 illustrates the top view of three typical outer-ray florets.
FIG. 12 illustrates the under view of three typical outer-ray florets.
FIG. 13 illustrates an array of typical inner-disc florets.
FIG. 14 illustrates a side of a typical inflorescence with buds and flowers in various stages of opening.

The chart used in the identification of colors described hereafter is The R.H.S. Colour Chart of The Royal Horticultural Society, London, England. In some instances more common color terms are provided and are to be accorded their usual dictionary significance. The plants described were grown at Nuaille, Trementines, France, in 20 cm. pots, three plants to a pot, were rooted during late May and were stopped in early July. All primary laterals were retained. The plants were grown outdoors until late September and then in a greenhouse having a minimum temperature of 15.5° C. These conditions approximate those commonly utilized for the production of decorative pot mums.

Classification:

*Botanical.—Dendranthema grandiflora, cv. 'Chazami'.*

*Commercial.*—Decorative pot mum.

Inflorescence

A. Capitulum:

*Type.*—Double daisy becoming daisy-eyed with age.

*Number of rows of involucral bracts.*—Five or less.

*Diameter across face.*—Approximately 4 to 5 cm. on average when fully expanded.

*Frequency.*—Corymbiform, tending to cylindrical.

*Outside bud coloration.*—Nearest Greyed-Red Group 178C, but somewhat more yellow.

B. Corolla of ray and disc florets:

*Receptacle.*—Small and conical raised.

*Disc florets.*—Tubular, yellow in coloration, and short to medium in overall length. Quite numerous, typically approximately 50 to 100 per flower, and a few are often scattered among the ray florets but most form a sub-discoid cluster at the apex of the receptacle which becomes visible as the flower head matures.

*Generaly tonality.*—Yellow.

*Color of disc florets.*—Before anther dehiscence, yellow-orange, and at anther dehiscence, orange.

*Color ray florets.*—Outer Side: At maturity most are Yellow Group 12B lightly tinged with red, near Greyed-Red Group 180A, between the ribs on the distal one-half. The inner-ray florets are near Yellow-Orange Group 14C but more red and with the red tints becoming weaker as the florets develop. Inner Side: At maturity most are near Yellow-Group 12A but considerably brighter with red tints near Greyed-Red Group 180A. The margin also is Greyed-Red Group 180A. The inner-ray florets are near Yellow-Orange Group 14B but are more red and the immature ray florets at the center are Greyed-Red Group 179A.

*Configuration ray florets.*—The longitudinal axis of the ray florets tends to be substantially straight. The length of the corolla tube of the ray florets is very short to short. The ray florets commonly have a cross-section that is weakly concave, there is no keel, and the ray florets tend to be strongly ribbed. The thickness of the ray florets is medium, and their surfaces are textured. The tips of the ray florets are dentate. The ray florets are approximately 2 cm. in length and approximately 1 cm. in width on average.

C. Reproductive organs:

*Androecium.*—Generally present with the disc florets and absent among the ray florets.

*Gynoecium.*—Generally present with the most disc florets and with most of the ray florets.

*Pollen.*—Formed in a slight quantity and golden-yellow in coloration.

*Fragrance.*—Typical of Chrysanthemum.

Plant

A. General appearance:

*Height.*—Short, and approximately 35 to 40 cm. in height on average.

B. Foliage:

*Color.*—Near Green Group 137A.

*Configuration.*—Lobed (as illustrated).

*Texture.*—Fleshy.

*Serration.*—Medium.

*Length of lower lobe.*—Medium to long.

*Shape of base of sinus.*—Rounded.

*Shape of base of leaf.*—Asymmetric, and tending to be truncate or weakly cordate.

*Claw in base of sinus between lateral lobes.*—Absent.

*Margins of sinus between lateral lobes.*—Converging.

*Apex.*—Mucronate.

*Stems.*—Strong, angular in cross section, present strong brittleness, Yellow-Green Group 146B in coloration, and commonly with anthocyanin coloration present in patches along the stem.

I claim:

1. A new and distinct cultivar of Chrysanthemum plant named 'Chazami', substantially as herein shown and described, which:

(a) exhibits in profusion attractive golden yellow double daisy blossoms, (b) is highly amenable to branching by pinching, (c) forms attractive dark green foliage, (d) assumes a short plant height, and (e) is particularly well suited for pot mum production on a natural production cycle.

* * * * * cm.
0
5
10
15
WALSH